US010040992B2

(12) United States Patent
Lee et al.

(10) Patent No.: US 10,040,992 B2
(45) Date of Patent: Aug. 7, 2018

(54) GUANINE CHEMILUMINESCENCE COMPOUND AND APPLICATIONS

(71) Applicant: LUMINESCENT MD, LLC, Gaithersburg, MD (US)

(72) Inventors: Ji Hoon Lee, Gaithersburg, MD (US); Sandy Cho, McLean, VA (US)

(73) Assignee: LUMINESCENT MD, LLC, Gaithersburg, MD (US)

( * ) Notice: Subject to any disclaimer, the term of this patent is extended or adjusted under 35 U.S.C. 154(b) by 0 days.

(21) Appl. No.: 14/890,316

(22) PCT Filed: May 9, 2014

(86) PCT No.: PCT/US2014/037463
§ 371 (c)(1),
(2) Date: Nov. 10, 2015

(87) PCT Pub. No.: WO2014/183013
PCT Pub. Date: Nov. 13, 2014

(65) Prior Publication Data
US 2016/0115381 A1    Apr. 28, 2016

Related U.S. Application Data

(60) Provisional application No. 61/822,031, filed on May 10, 2013.

(51) Int. Cl.
| | | |
|---|---|---|
| *C07H 21/02* | (2006.01) | |
| *C07H 21/04* | (2006.01) | |
| *C09K 11/07* | (2006.01) | |
| *C07D 473/18* | (2006.01) | |
| *C09K 9/02* | (2006.01) | |
| *C07D 491/22* | (2006.01) | |
| *G01N 21/76* | (2006.01) | |
| *G01N 33/543* | (2006.01) | |
| *H01F 1/01* | (2006.01) | |
| *G01N 21/75* | (2006.01) | |

(52) U.S. Cl.
CPC .......... *C09K 11/07* (2013.01); *C07D 473/18* (2013.01); *C07D 491/22* (2013.01); *C07H 21/02* (2013.01); *C07H 21/04* (2013.01); *C09K 9/02* (2013.01); *G01N 21/76* (2013.01); *G01N 33/54306* (2013.01); *H01F 1/01* (2013.01); *C09K 2211/1007* (2013.01); *C09K 2211/1074* (2013.01); *C09K 2211/1077* (2013.01); *C09K 2211/1466* (2013.01); *G01N 2021/757* (2013.01)

(58) Field of Classification Search
CPC .... C07D 473/18; C07D 491/22; C07H 21/02; C07H 21/04; C09K 11/07

USPC ..... 435/6.1, 6.11, 6.12, 6.18, 19, 91.1, 91.2, 435/91.31, 6.19; 536/23.1, 24.3, 24.33, 536/25.3, 25.32, 26.71, 24.5; 436/501

See application file for complete search history.

(56) References Cited

U.S. PATENT DOCUMENTS

2015/0191796 A1*  7/2015  Liew .................... C12Q 1/6886
506/9

FOREIGN PATENT DOCUMENTS

CN           102050823       *   5/2011

OTHER PUBLICATIONS

Kai et al, Analytica Chim. Acta, vol. 381, pp. 155-163 (1999).*
Meng et al, Huadong Ligong Daxue Xuebao, Ziran Kexueban, vol. 38, No. 3, pp. 334-339 (2012).*
Jeevagan et al., "Electrochemical determination of guanosine 5'-monophosphate using the electropolymerized film of non-peripheral amine substituted nickel(II) phthalocyanine modified electrode", Electrochimica Acta, vol. 95, 2013, pp. 246-250.
Kai et al., "A chemiluminescence derivatization method for detecting nucleic acids and DNA probes using a trimethoxyphenylglyoxal reagent that recognizes guanine", Analytica Chimica Acta, vol. 381, 1999, pp. 155-163.
Li et al., "A sensitive graphene oxide-DNA based sensing platform for fluorescence "turn-on" detection of bleomycin", Chem. Commun., vol. 48, 2012, 127-129.
Mei et al., "A novel flow-injection chemiluminescence system for the determination of guanine", Luminescence, vol. 20, 2005, pp. 307-310.
Sato et al., "Chemiluminescence Method for Determining Adenine after a Reaction with an Alkylglyoxal Compound", Analytical Sciences, vol. 13, Feb. 1997, pp. 59-65.
Qu et al., "Natural DNA-Modified Graphene/Pd Nanoparticles as Highly Active Catalyst for Formic Acid Electro-Oxidation and for the Suzuki Reaction", ACS Appl. Mater. Interfaces, vol. 4, 2012, 5001-5009.
Yang et al., "Superparamagnetic graphene oxide-Fe3O4 nanoparticles hybrid for controlled targeted drug carriers", Journal of Materials Chemistry, vol. 19, 2009, pp. 2710-2714.
Zhao et al., "The fluorescence enhancement effect of the Tb—Gd-guanosine-5'-triphosphate-phen system and its analytical application", Anal. Bioanal. Chem., vol. 380, 2004, pp. 104-107.

* cited by examiner

*Primary Examiner* — Jane Zara
(74) *Attorney, Agent, or Firm* — Birch, Stewart, Kolasch & Birch, LLP

(57) ABSTRACT

Chemiluminesescence is emitted from a reaction between phenylglyoxal derivatives and guanine. This chemiluminescence can be used in CRET for the detection of one or more analytes of interest. Chemical pathways depicting the chemiluminescent reaction and intermediates produced therein are shown, as are novel nanoparticles for use in the present methods and compositions.

4 Claims, 10 Drawing Sheets

FIG 3
FIG 3A
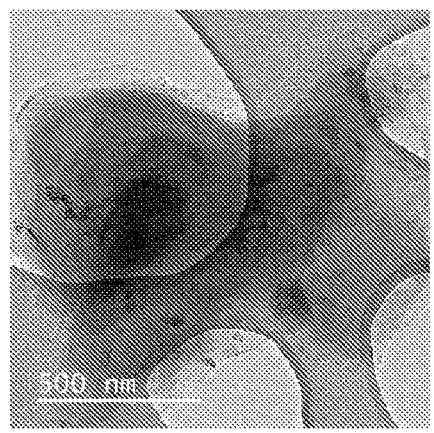
FIG 3B
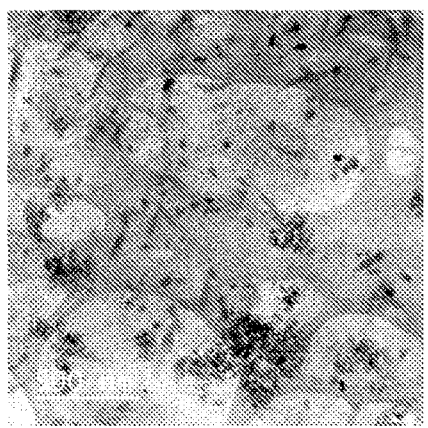

GUANINE CHEMILUMINESCENCE COMPOUND AND APPLICATIONS

This application is the National Phase of PCT International Application No. PCT/US2014/037463, filed on May 9, 2014, which claims priority under 35 U.S.C. 119(e) to U.S. Provisional Application No. 61/822,031, filed on May 10, 2013, all of which are hereby expressly incorporated by reference into the present application.

SEQUENCE LISTING

A sequence listing is being concurrently submitted in text form and paper form. The file name is 2014May 8 Sequence Listing 6312-0104PW01.txt, created on May 8, 2014, and has a size of 1450 bytes. The entire contents of 2014May 8 Sequence Listing 6312-0104PW01.txt are hereby expressly incorporated by reference.

FIELD OF INVENTION

This invention involves chemiluminescence emitted from the reaction between phenylglyoxal derivatives and guanine, one of the four main nucleobases found in the nucleic acids DNA and RNA, in the presence of weak or strong bases as well as its applications.

BACKGROUND

Glow and weak chemiluminescence, emitted from the multiple and slow reaction pathways between phenylglyoxal derivatives and guanine, has been reported since early 1990's. The disadvantages of the chemiluminescence made it difficult to apply as a detection method capable of sensing trace levels of analytes.

Rapid and strong chemiluminescence emitted from the non-stop reaction pathway of phenylglyoxal derivatives and guanine under neutral or basic condition was observed. Based on the advantages of the chemiluminescence, various biosensors capable of quantifying trace levels of analytes were developed.

BRIEF DESCRIPTION OF THE DRAWINGS

FIG. 3: TEM images of pure graphene oxide (a) and magnet Fe3O4-graphene oxide (b).

DETAILED DESCRIPTION

Figure 1:
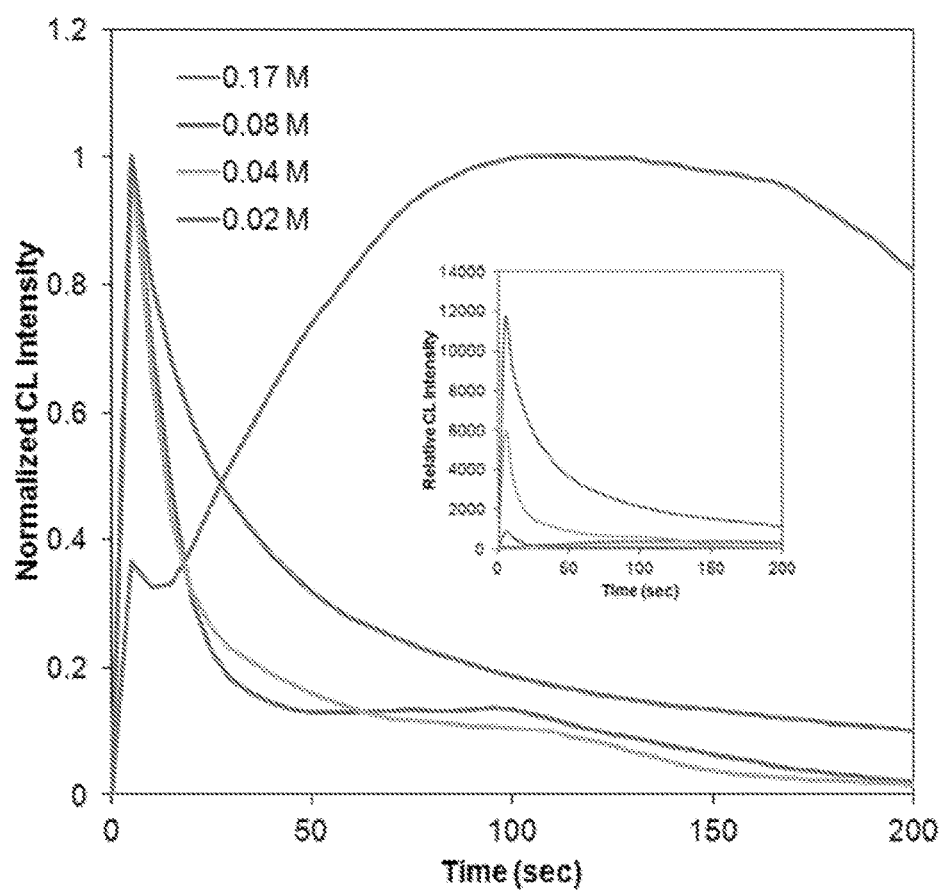
FIG. 1: Concentration effect of tertrapropyl ammonium hydroxide (TPA) in guanine chemiluminescence. Condition: [ssDNA]=1 μM in $H_2O$, [TMPG]=0.02M in DMF.

The present inventions consist of a new guanine chemiluminescence reaction pathway using various phenylglyoxal derivatives and bases as well as its application as a highly sensitive detection method of sensors capable of quantifying trace levels of analyte such as biomarkers, drug, environmental toxic materials and food-borne pathogens.

Guanine, a main compound of chemiluminescence, is one of the four main nucleobases of single strand DNA and RNA. Guanine has the following structure:

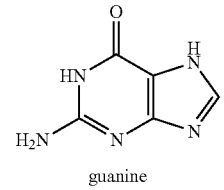 [SMILES: Nc1nc2nc[nH]c2c(=O)[nH]1]

guanine

Analogs of guanine of interest may also be used. Such analogs may include artificial nucleotides/nucleosides, methylated nucleotides/nucleosides, methylated ribonucleotides/nucleosides, isoguanine, morpholinoguanine, 2'-O-methyl substituted guanine, etc.

Phenylglyoxal has the following structure:

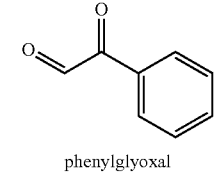

phenylglyoxal

Phenylglyoxal, its analogs, and its derivatives causes a release of energy, aka chemiluminescence when it reacts with guanine. Suitable phenylglyoxal derivatives include acetyl, oxy, methoxy, or C1-C6 linear or branched alkyl substituents on the phenyl ring. Phenylglyoxal derivatives preferably include phenylglyoxal, 3- or 4-methoxyphenylglyoxal, 3,4- or 3,5-dimethoxyphenylglyoxal, 3,4,5-trimethoxyphenylglyoxal.

Bases are catalysts of guanine chemiluminescence. Suitable bases for use in the present reactions include alkaline buffers and basic compounds. The alkaline buffers are not particularly limited, and can include ammonium phosphate buffers, $K_2HPO_4$ buffers, and $Na_2HPO_4$ buffers. The basic compounds are not particularly limited but include tetra-n-methyl ammonium phosphate, tetra-n-ethyl ammonium phosphate, tetra-n-propyl ammonium phosphate (TPA), and tetra-n-butyl ammonium phosphate and combinations thereof.

Aptamers are oligonucleic acid molecules having at least a single stranded section that binds a specific target molecule. Nucleic acid is generally used herein to include both deoxyribonucleic acids and ribonucleic acids. The terms "nucleoside", "nucleoside monophosphate" and "nucleotide" have their conventional meanings regarding the base and phosphate structures, but again applies to ribonucleotides or deoxyribonucleotides.

Aptamers may have a length ranging from 10 nucleotides to 100 nucleotides, more preferably from about 15 nucleotides to 60 nucleotides. Preferably the aptamer contains at least 1 guanine, at least 2, at least 3 at least 4, at least 5, at least 6, at least 7, at least 8, at least 9 guanines, at least 10 guanines, at least 11 guanines, at least 12 guanines, at least 13 guanines, at least 14 guanines . . . at least 50 guanines (inclusive). In one embodiment, the number of guanines is accounted as a percentage of total nucleotides in the aptamer. Accordingly, in this embodiment, the aptamer contains at least at least 10% guanines, at least 15% guanines, at least 20% guanines, at least 25% guanines, at least 30% guanines, at least 35% guanines, at least 40% guanines, at least 45% guanines, or at least 50% guanines, at least 55% guanines, at least 60% guanines, at least 65% guanines, or at least 70% guanines. In a further aspect of this embodiment, the aptamer contains approximately 20% guanines, approximately 25% guanines, approximately 30% guanines, approximately 35% guanines, approximately 35% guanines, approximately 40% guanines, approximately 45% guanines, approximately 50% guanines, approximately 55% guanines, approximately 60% guanines, approximately 65% guanines, approximately 70% guanines, or approximately 75% guanines. In a preferred aspect, the aptamer includes approximately 60% guanines.

Aptamers may or may not be labeled or conjugated to labels, dyes, reporters, or other compounds used in detection of nucleic acids. In particular, the aptamers of the present invention used for quantifying various analytes include label-free single stranded DNA or RNA containing multiple guanines and single stranded DNA or RNA conjugated with fluorescent dye.

Guanine chemiluminescence is applied as a detection method of aptasensors capable of sensing trace levels of analyte. Analytes of interest include proteins, inorganic and organic molecules, and other compounds of interest. In one embodiment, the aptamers used in the present methods detect analytes including biomarkers, drugs, environmental toxic materials and food-borne pathogens. In one aspect of the embodiment, the biomarker is a tumor marker, a neurological disease marker, a marker of cardiovascular disease, a marker for auto-immune disease, a marker of inflammation, a marker of diabetes (Type I and Type II), a marker for infectious disease, or a marker of other metabolic disease. In a further aspect of the embodiment, the biomarker is PSA. In a further aspect, the biomarker is thrombin. In another embodiment, the environmental toxic material or food-borne pathogen is a bacterium, a pesticide, a prion, a poison. In a further embodiment, the environmental toxic material or food-borne pathogen is tetrodotoxin, ricin, scrombotoxin, abrin, botulinum neurotoxins, enterotoxins (such as *Staphylococcus aureus* enterotoxins A, B, and F), saxitoxin, mycotoxins (such as DAS), T-2 toxin, tetanus, taipoxin, diphtheria toxin etc. In one embodiment, the bacteria are *E. Coli, listeria, salmonella, vibrio* etc.

Applications of guanine chemiluminescence are sandwich assays. Sandwich immunoassays may use a specific capture antibody and a using the present methods as a reporter aptamer. Aptamer only sandwich assays may use a specific capture aptamer and use the present methods with a second aptamer acting as a reporter aptamer. Further, the present methods may be used with one or more aptamers simultaneously acting as both capture agent and reporter agent. Further there are various analytical methods using only aptamer(s), capable of rapidly capturing a specific target material in a sample, with/without being immobilized to a substrate. In one embodiment, the substrate may be a monolithic column, nanoparticles, a plate (such as a multi-well plate), a slide, a membrane, or a dish.

In one embodiment, nanoparticles used to develop aptasensor and sandwich immunoassay with guanine chemiluminescence detection may include gold nanoparticles, silver nanoparticles, silica nanoparticles, coated or uncoated polymer nanoparticles (e.g., polylactic acid/polyethylene glycol (PLA-PEG) or polylactide-co-glycolide/polyethylene glycol (PLGA-PEG), optionally coated with lipids, sugars etc.), magnetic $Fe_3O_4$ carbon nanotubes and magnetic $Fe_3O_4$ graphene oxide. Methods of making gold nanoparticles, silver nanoparticles, silica nanoparticles, coated or uncoated polymer nanoparticles are recognized in the art, but methods of making magnetic $Fe_3O_4$ carbon nanotubes and magnetic $Fe_3O_4$ graphene oxide are novel.

To make the magnetic $Fe_3O_4$ graphene oxide $FeCl_2$ and $FeCl_3$ are dissolved in deionized water at a ratio ranging from 1:1 to 1:10, more preferably 1:4 and optionally mixed at a raised temperature (ranging from room temperature to 150° C., preferably 85° C.). Graphene oxide is prepared in deionized water and mixed with the $FeCl_2$ and $FeCl_3$ at a raised temperature (ranging from room temperature to 150° C., preferably 85° C.) Ammonium hydroxide is added to the mixture of $FeCl_2$ and $FeCl_3$ and grapheme oxide and stirred for an extended period (from 15 minutes to 2 hours, preferably about 1 hour, preferably 50 minutes) again at a raised temperature (ranging from room temperature to 150° C., preferably 85° C.). The mixture is cooled at room temperature and washed with water to obtain the magnetic $Fe_3O_4$-graphene oxide. It may be subsequently stored in a refrigerator.

To obtain the $Fe_3O_4$-carbon nanotubes, single-, double-, or multi-walled carbon nanotubes (1 mg/ml) were prepared in deionized water. $FeCl_2$ and $FeCl_3$ are dissolved in deionized water at a ratio ranging from 1:1 to 1:10, more preferably 1:4, and optionally mixed at raised temperature. The $FeCl_2$ and $FeCl_3$ are added to a container having the carbon nanotubes, and mixed at a raised temperature (ranging from room temperature to 150° C., preferably 85° C.). Ammonium hydroxide is added to the mixture of $FeCl_2$ and $FeCl_3$ and carbon nanotubes and stirred for an extended period (from 15 minutes to 2 hours, preferably about 1 hour, preferably 50 minutes) again at a raised temperature (ranging from room temperature to 150° C., preferably 85° C.). The mixture is cooled at room temperature and washed with water to obtain the magnetic $Fe_3O_4$-carbon nanotubes. Then, the resultant magnetic $Fe_3O_4$-carbon nanotubes in the container may be stored it a refrigerator.

Fluorescent dyes suitable to be conjugated to the aptamer for use in the present methods are not particularly limited. In one embodiment the fluorescent dye is pacific blue, fluorescein, 6-FAM, Cy 3, Cy 3.5, Cy 5, Cy 5.5, HEX, TET, VIC, NED, JOE, ROX, Texas Red, Rhodamine Green, Rhodamine Red, TEX 615 and so on. As the art of fluorescent labels and dyes is well understood, it is expected that any fluorescent dye would be useful in the present reactions.

Methods of the present invention include combining a sample suspected of having a specific analyte with phenylglyoxal (or a derivative thereof) and a guanine-containing aptamer which binds the specific analyte in the presence of a base or subsequently adding a base. Luminescence is then measured.

The amount of single stranded DNA or RNA (i.e., the aptamer) in the sample can range from 1 pM to 1 mM. In one embodiment the amount of aptamer in the mixture is 0.1 μm to 100 μM. In a further embodiment the amount of aptamer is approximately 0.5 μM to 10 μM. In a preferred embodiment the amount of aptamer is approximately 0.5μ to 1 μM.

The amount of phenylglyoxal or derivative thereof in the mixture ranges from about 0.1 μM to 2000 μM. In one embodiment the amount of phenylglyoxal in the mixture ranges from about 1 μM to 75 μM or about 10 μM to 50 μM. In a preferred aspect, the amount of phenylglyoxal or derivative thereof in the mixture is about 20 μM.

The amount of base in the mixture ranges from 0.1 mM to 10 M. In one embodiment the amount of base is about at least 0.01 mM, at least 0.05 mM, at least 0.1 mM, at least 0.5 mM, at least 0.75 mM, at least 1 mM, at least 1.25 mM, at least m 1.5 mM, at least 1.75 mM, at least 2.0 mM, at least 5 mM, at least 10 mM, at least 15 mM, at least 20 mM, at least 25 mM, at least 30 mM, at least 35 mM, at least 35 mM, at least 40, mM at least 50 mM, at least 55 mM, at least 60 mM, at least 65 mM, at least 70 mM, at least 75 mM, at least 80 mM, at least 85 mM, at least 90 mM, at least 95 mM, at least 100 mM, at least 0.2 M, at least 0.4 M, at least 0.5 M, at most 1M or at most 2M. In one embodiment the amount of base in the mixture ranges from about 0.01 M to 5 M, 0.05 M to 2.5 M, 0.2 M to 2 M, or 0.1 M to 1M. In one aspect, the amount of base is 0.01 M, 0.02M, 0.04 M, 0.08 M, 0.16 M, 0.17 M, 1 M, or 2 M. In one further aspect the amount of base ranges from 5-100 mM. Phenylglyoxal and derivatives thereof may be dissolved in miscible solvents, to permit them to mix with aqueous solutions. Miscible solvents are known, but in particular include dimethylformamide (DMF), DMSO, dimethylacetamide, acetone, acetonitrile, 2-methyltetrahydrofuran, methanol, or others.

Luminescence may be measured by conventional techniques. The period for measurement may be less than a second up to five minutes. In one embodiment, luminescence is measured for less than 5 seconds, less than 10 seconds, less than 15 seconds, less than 30 seconds, less than 45 seconds, less than 1 minute, less than 90 seconds, less than 120 seconds, less than 150 seconds, less than 165 seconds, less than 180 seconds, less than 200 seconds, less than 210 seconds, less than 240 seconds, or less than 270 seconds. In another embodiment, the luminescence is measured for at least 1 second, at least 2 seconds, at least 3 seconds, at least 4 seconds, at least 5 seconds, at least 10 seconds, at least 15 seconds, at least 20 seconds at least 30 seconds, at least 45 seconds, at least 50 seconds, at least 55 seconds, at least 60 seconds, at least 90 seconds, at least 120 seconds, at least 150 seconds, or at least 200 seconds. In one aspect, the luminescence is measured for 1-60 seconds, 1-40 seconds, 1-30 seconds, 1-20 seconds, or 1-10 seconds. In a preferred embodiment, luminescence is measured for 5 seconds.

The present method can be combined with multiple different types of fluorescent labels to simultaneously measure multiple analytes. This may be done for example by using a luminometer with multiple photomultipliers with different filters on the photomultipliers to measure emissions in a certain range.

Furthermore the present methods are highly sensitive, detecting analytes at concentrations such as 1 ng/ml to 150 ng/ml. The present methods correlate well to detection by other chemiluminescent means, such as using 1,1'-oxalyldiimidazole chemiluminescent enzyme assays.

Without being bound to any particular theory, upon mixing the guanine containing DNA, the phenylglyoxal and base, it is believed that the interaction between guanine and phenylglyoxal (and its derivatives) proceeds directly to generate two different high energy intermediates, listed in scheme 1 as X and Y:

Scheme 1 Two different pathways emitting light in Guanine-CL reaction.

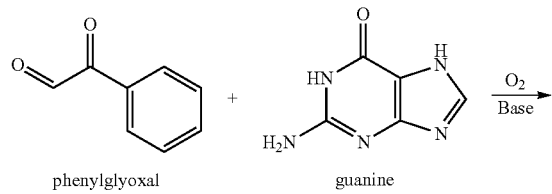

phenylglyoxal    guanine

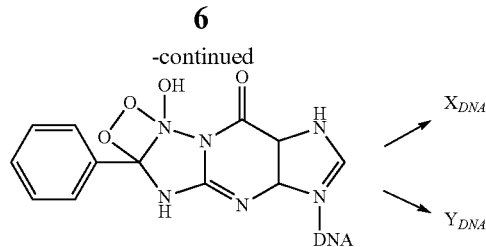

In the absence of a fluorescent labeled aptamer or fluorescent dye, when a higher concentration of base is added, then a single decay curve of chemiluminescence is observed (see, FIG. 1, 0.02 M base). At higher concentrations of base, a dual decay curve is observed (see FIG. 1). Without being bound by any particular theory, it is hypothesized that there are two different reaction pathways that lead to chemiluminescence of guanine. It is hypothesized that these two pathways generate two different high-energy intermediates whose potential structures are shown below in scheme 2.

Scheme 2 Possible structures of high-energy intermediates X and Y, wherin TPA is the base tetra-n-propyl ammonium phosphate.

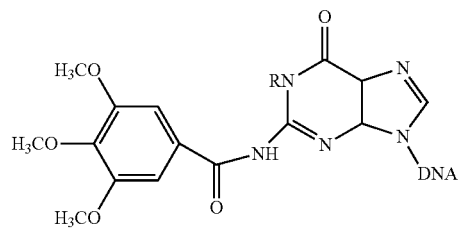

X: R = H under the neutral condition (low concentration of TPA)
Y: R = ununder the basic condition (high concentration of TPA)

Figure 2:
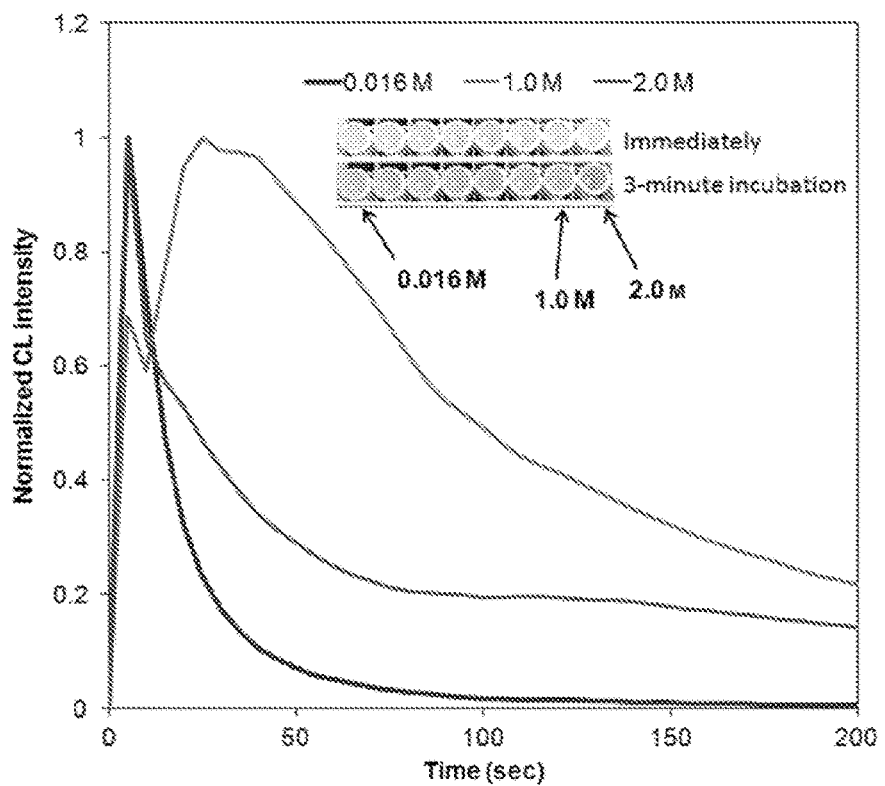
FIG. 2: Competitive and consecutive guanine chemiluminescence in the presence of various concentrations of TPA. Condition: [ssDNA]=1 μM in $H_2O$, [TMPG]=0.02 M in DMF.

The X intermediate is generated quickly and decays quickly at low concentrations of base. The Y intermediate is generated more slowly and decays more slowly at high concentrations of base. It is believed that the X intermediate also resonates with fluorescent labels conjugated to the aptamers, generating a much more intense signal. As shown by FIG. 2, at higher concentrations of base there is a color shift in the resultant products from pale yellow to dark yellow (1 M base) to pink (2 M base) after a short incubation period.

The following examples serve to illustrate the invention. These examples are in no way intended to limit the scope of the present methods.

EXAMPLES

The following non-limiting examples are provided for illustrative purposes only in order to facilitate a more complete understanding of the disclosed subject matter. These examples should not be construed to limit any of the embodiments described in the present specification, including those pertaining to the methods for generating guanine chemiluminescence, detecting an analyte and kits comprising the components necessary to perform the disclosed methods.

Example A

Competitive and Consecutive Guanine Chemiluminescence Reactions

1 µM label-free single strand DNA and 1 µM single strand DNA conjugated with 6-FAM were prepared in deionized water.

3,4,5-trimethoxyphenylglyoxal (TMPG, 20 mM) was prepared in N,N-dimethylformamide (DMF).

Various concentrations of tetra-n-propyl ammonium phosphate (TPA) were prepared in deionized water.

6-FAM (1 μM) was prepared in deionized water.

Procedure

Label free single strand DNA (or single strand DNA conjugated with 6-FAM, 20 μl), TPA (10 μl), and TMPG (100 μl) were mixed in a borosilicate test tube, and CL emission was immediately measured for 200 seconds using LB 9507 Luminometer.

observed in the presence of 1.0 M TPA indicates that the second reaction pathway shown in Scheme 1 is dominant. Thus, it is possible that Guanine-CL in the presence of 2.0 M TPA has a single-decay curve generated from the second reaction pathway shown in Scheme 1.

In addition, the picture of FIG. 2 shows that the color (pale yellow or colorless) of product(s) formed from the first reaction pathway (0.016 M TPA) was different from those in the presence of 1.0 (dark yellow) and 2.0 M (pink) after 3

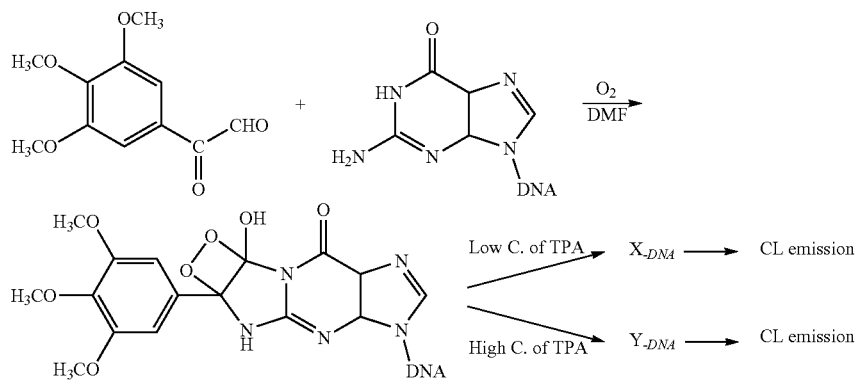

Scheme 3 Two different pathways emitting light in Guanine-CL reaction.

As shown in FIG. 1, the shape of Guanine-CL is dependent on the concentration of TPA prepared in $H_2O$. In other words, the shape of Guanine-CL in the presence of 0.02 M TPA has a single-decay curve. However, the shapes of Guanine-CL observed with the increase of TPA concentration have dual-decay curves. The results shown in FIG. 1 indicate that Guanine-CL is generated from high-energy intermediates, X and Y, competitively formed in two different reaction pathways as shown in Scheme 3.

The results in FIG. 2 are consistent with those in FIG. 1. Guanine-CL in the presence of 0.016 M TPA has a single-decay curve generated from the first reaction pathway shown in scheme 1. Guanine-CL in the presence of 1.0 M TPA has a dual-decay curve competitively generated from two different reaction pathways. Also, the dual-decay curve minutes of incubation. These results also indicate that Guanine-CL observed in the presence of a certain concentration of TPA is generated from competitive reactions through two different pathways.

The results shown in FIG. 2 indicates that Guanine-CL generated from two different reaction pathways can be applied as a detection method of various sensors capable of quantifying a target sample such as biomarkers, drug, environmental toxic materials and food-borne pathogens.

TABLE 1

Inter- and intra-interaction between 6-FAM and high-energy intermediates formed in Guanine-CL

| | ssDNA only [a] | | | ssDNA and 6-FAM [b] | | | ssDNA conjugated 6-FAM only [c] | | |
|---|---|---|---|---|---|---|---|---|---|
| | $I_{max}$[d] | $\tau_{max}$[e] | $\tau_{1/e}$[e] | $I_{max}$[d] | $\tau_{max}$[e] | $\tau_{1/e}$[e] | $I_{max}$[d] | $\tau_{max}$[e] | $\tau_{1/e}$[e] |
| X [f] | 1 | 5 | 20 | 0.80 | 5 | 18.5 | 86.0 | 5 | 125 |
| Y [g] | 1 | 5 | 37 | 0.84 | 5 | 33 | 0.83 | 5 | 32 |

[a] ssDNA (4.44 nM, 5-GGTTGGTGTGGTTGG-3 (SEQ ID NO: 1)) without 6-FAM
[b] ssDNA (4.44 nM, 5-GGTTGGTGTGGTTGG-3 (SEQ IDNO: 1)) and FAM (4.44 nM) for the study of inter-interaction between 6-FAM and emitters formed in TMPG-CL reaction
[c] ssDNA conjugated with 6-FAM (4.44 nM, 5-FAM-GGTTGGTGTGGTTGG-3 (SEQ ID NO: 1)) for the study of intra intra-interaction between 6-FAM and high-energy intermediates formed in TMPG-CL reaction.
[d] Maximum intensity normalized with that measured in the presence of ssDNA only.
[e] Unit: second
[f] [TMPG] = 2.45 x $10^{-2}$ M, [TPA] = 0.02 M
[g] [TMPG] = 1.18 x $10^{-4}$ M, [TPA] = 2.0 M Based on the results shown in FIG. 2, it is possible that two peaks competitively generated from the two high-energy intermediates formed in Guanine-CL reaction were separated using the concentration ratio between TMPG and TPA in the presence of ssDNA as shown in Table 1. In other words, the high-energy intermediate (X) was predominantly formed in Guanine-CL in the presence of $2.45 \times 10^{-2}$ M TMPG and 0.02 M TPA, whereas the single CL peak observed in the presence of $1.18 \times 10^{-4}$ M TMPG and 2.0 M TPA comes from the high-energy intermediate (Y).

Table 1 shows that the time ($\tau_{max}$) necessary for attaining maximum intensity ($I_{max}$) measured under the Guanine-CL reaction condition to form X in the presence of ssDNA only is the same as that under the Guanine-CL reaction condition to form Y. However, half-decay time ($\tau_{1/e}$) necessary for attaining 1/e of $I_{max}$ under the former condition was faster than that under the latter condition. The results shown in Table 1 are consistent with those shown in FIG. 2.

As shown in Table 1, $I_{max}$ measured under the Guanine-CL reaction condition to form X in the presence of ssDNA and 6-FAM was slightly lower than that in the presence of ssDNA only. However, $\tau_{max}$ and $\tau_{1/e}$ under the former condition were similar to those of under the latter condition. In addition, the trend observed under the Guanine-CL reaction condition to form Y was the same as the results obtained under Guanine-CL reaction condition to form X. These results indicate that 6-FAM individually added in Guanine-CL reaction acts as a quencher or does not apparently interact with X and Y.

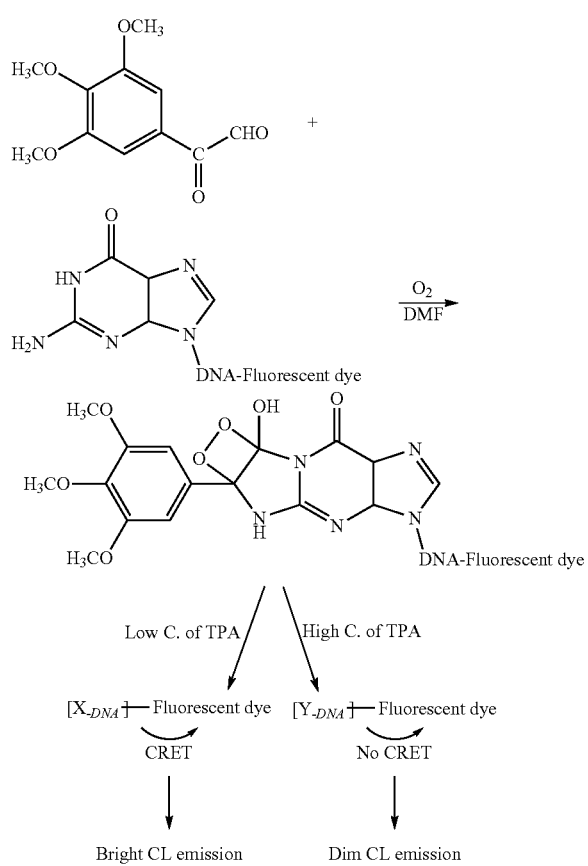

Scheme 4 Two different Guanine-CL reactions in the presence of ssDNA conjugated with fluorescent dye.

As shown in Table 1, $I_{max}$ in Guanine-CL reaction in the presence of ssDNA-conjugated FAM Guanine-CL reaction condition to form X is 86 times higher than that in Guanine-CL reaction in the presence of ssDNA only. Also, $\tau_{1/e}$ under the former condition was about 6.3 times longer than that under the latter condition. However, $\tau_{max}$ under the former condition was the same as that under the latter condition within the acceptable error range. The results indicate that X formed in Guanine-CL reaction in the presence of ssDNA-conjugated 6-FAM transfers energy to 6-FAM due to the intra-interaction between X and 6-FAM. Thus, bright light observed in Guanine-CL reaction in the presence of ssDNA-conjugated FAM comes from strong emission of 6-FAM receiving energy from X, formed in this condition, based on the principle of chemiluminescent resonance energy transfer (CRET) as shown in Scheme 4.

As shown in Table 1, however, the shape of CL observed in Guanine-CL reaction in the presence of ssDNA-conjugated 6-FAM to form Y is same as that obtained in Guanine-CL reaction in the presence of ssDNA and 6-FAM. The result indicates that 6-FAM bound with ssDNA in this condition cannot receive energy from Y to emit bright light as well acts as a dynamic quencher due to the intra-interaction between Y and 6-FAM.

Role of Fluorescent Dye Bound with ssDNA in Guanine-CL Reaction to Form X

1 μM label-free single strand DNA was prepared in deionized water.

1 μM single strand DNA conjugated with fluorescent dye (e.g., Pacific blue, 6-FAM, fluorescein, Joe, ROX, Texas Red, Cy 3.5) were prepared in deionized water.

3,4,5-trimethoxyphenylglyoxal (TMPG, 1 mM) was prepared in N,N-dimethylformamide (DMF).

Various concentrations of tetra-n-propyl ammonium phosphate (TPA) were prepared in deionized water.

Procedure

Label free single strand DNA (or single strand DNA conjugated with fluorescent dye, 20 μl), TPA (10 μl), and TMPG (100 μl) were mixed in a borosilicate test tube, and CL emission was immediately measured for 200 seconds using LB 9507 Luminometer.

TABLE 2

Chemiluminescent resonance energy transfer (CRET) between X and fluorescent dye bound with ssDNA

|  | $I_{max}$ | $\tau_{max}$ | $\tau_{1/e}$ |
| --- | --- | --- | --- |
| ssDNA only | 1 | 5 | 35 |
| ssDNA-conjugated Pacific Blue | 103.3 | 5 | 21 |
| ssDNA-conjugated 6-FAM | 171.7 | 5 | 65 |
| ssDNA-conjugated fluorescein | 140.2 | 5 | 60 |
| ssDNA-conjugated Joe | 5.9 | 5 | 40 |
| ssDNA-conjugated ROX | 8.8 | 5 | 45 |
| ssDNA-conjugated Texas Red | 1.4 | 5 | 42 |
| ssDNA-conjugated Cy3.5 | 34.1 | 5 | 47 |

Condition: [TMPG] = 1.0 mM in DMF, [TPA] = 20 mM in deionized water

As shown in Table 2, X formed in Guanine-CL reaction can transfer energy to fluorescent dye bound with ssDNA based on the principle of CRET. Thus, $I_{max}$ and $\tau_{1/e}$ in guanine-CL reaction to form X were dependent on the property of fluorescent dye bound with ssDNA even though $\tau_{max}$ was similar within the acceptable error range (±5%). In addition, the color of light emitted in Guanine-CL reaction to form X was detemined based on the specific emission wavelength of fluorescent dye bound with ssDNA. The results indicate that multiple targets in a sample can be simultaneously quantified using Guanine-CL reaction to form X and several types of ssDNAs conjugated different fluorescent dyes capable of binding with specific target in a sample.

Synthesis of Magnetic Nanoparticles

C-1. Synthesis of Magnetic $Fe_3O_4$-graphene Oxide

The mixture of $FeCl_2$ (10 mg) and $FeCl_3$ (30 mg) were dissolved in deionized water (10 ml)

Graphene oxide (1 mg/ml) was prepared in deionized water.

Ammonium hydroxide (30%) was purchased from Sigma-Aldrich.

Procedure

The mixture (500 µl) of $FeCl_2$ and $FeCl_3$ was added in a 1.5 ml-centrifuge tube containing graphene oxide (500 µl). The centrifuge tube was inserted into a shaker at 85° C. Ammonium hydroxide (20 µl) was injected into the centrifuge tube. The mixture of the centrifuge tube was stirred rapidly at 85° C. for 50 minutes. The centrifuge tube was cooled at room temperature. Then, magnetic $Fe_3O_4$-graphene oxide in the centrifuge tube was washed multiple times with deionized water and stored at a refrigerator to use as a stock solution. TEM images of FIG. 3 indicate differences between pure graphene oxide and magnetic $Fe_3O_4$-graphene oxide.

C-2. Synthesis of Magnetic $Fe_3O_4$-carbon Nanotubes

The mixture of $FeCl_2$ (10 mg) and $FeCl_3$ (30 mg) were dissolved in deionized water (10 ml)

Single-, double-, or multi-walled carbon nanotubes (1 mg/ml) was prepared in deionized water.

Ammonium hydroxide (30%) was purchased from Sigma-Aldrich.

Procedure

Figure 4:
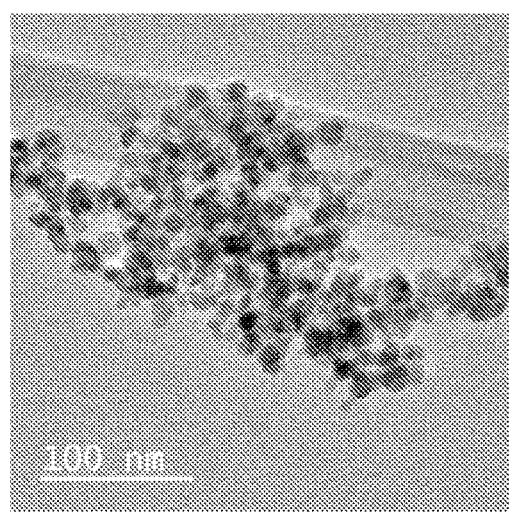
FIG. 4: TEM image of magnetic $Fe_3O_4$-carbon nanotubes

The mixture (500 µl) of $FeCl_2$ and $FeCl_3$ was added in a 1.5 ml-centrifuge tube containing carbon nanotubes (500 µl). The centrifuge tube was inserted into a shaker at 85° C. Ammonium hydroxide (20 µl) was injected into the centrifuge tube. The mixture of the centrifuge tube was stirred rapidly at 85° C. for 50 minutes. The centrifuge tube was cooled at room temperature. Then, magnetic $Fe_3O_4$-carbon nanotubes in the centrifuge tube was washed multiple times with deionized water and stored at a refrigerator to use as a stock solution. FIG. 4 shows the TEM image of magnetic $Fe_3O_4$-carbon nanotubes.

Quantification of Tumor Marker Using a Aptasensor with Guanine-CL and Magnetic Graphene Oxide Various concentrations of prostate specific antigen (PSA, a tumor marker) were prepared in human serum.

A specific DNA aptamer (1 µM) conjugated with 6-FAM (PSA aptamer: 5'-TTT TTA ATT AAA GCT CGC CAT CAA ATA GCT GGG GG-6-FAM-3', SEQ ID NO: 2) capable of rapidly capturing PSA, was prepared in deionized water.

Magnetic $Fe_3O_4$-graphene oxide stock solution was 5-fold diluted in deionized water.

Magnetic $Fe_3O_4$-carbon nanotube stock solution was 5-fold diluted in deionized water.

0.02 M TPA was prepared in deionized water.

1 mM TMPG was prepared in DMF.

Procedure

PSA (50 µl) and aptamer (50 µl) were mixed in a 1.5-ml centrifuge tube and incubated for 30 minutes at room temperature.

The mixture (20 µl) was inserted into a borosilicate test tube containing TPA (10 µl).

TMPG (100 µl) was added in the test tube and measured immediately CL emission for 20 seconds using a luminometer.

Results

Figure 5:
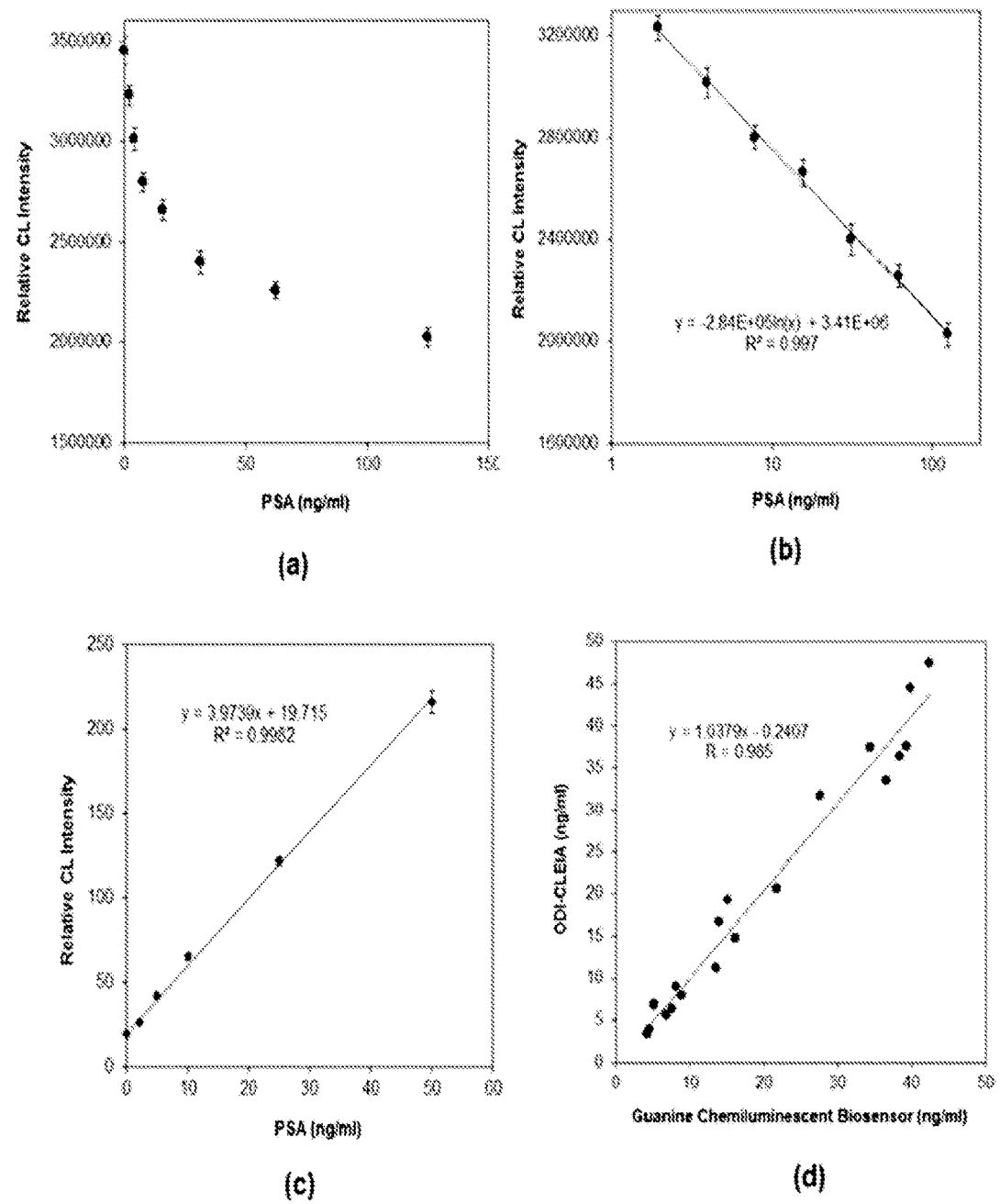
FIG. 5: (a and b) Calibration curve for the quantification of PSA antigen using guanine chemiluminescent biosensor, (c) Calibration curve for the quantification of PSA antigen using 1,1'-oxalyldiimidazole chemiluminescent enzyme immunoassay (ODI-CLEIA), (d) Correlation between guanine chemiluminescent biosensor and ODI-CLEIA.

With the increase of PSA, CL emission was decreased because PSA aptamer bound with PSA cannot emit light due to the CRET between X and PSA. PSA in human serum was quantified with a wide linear calibration curve shown in FIG. 5 (b). The correlation between the new method and conventional immunoassay (e.g., 1,1'-oxalyldiimidazole (ODI) chemiluminescent enzyme immunoassay) was good within acceptable error range as shown in FIG. 5 (d).

Figure 9:
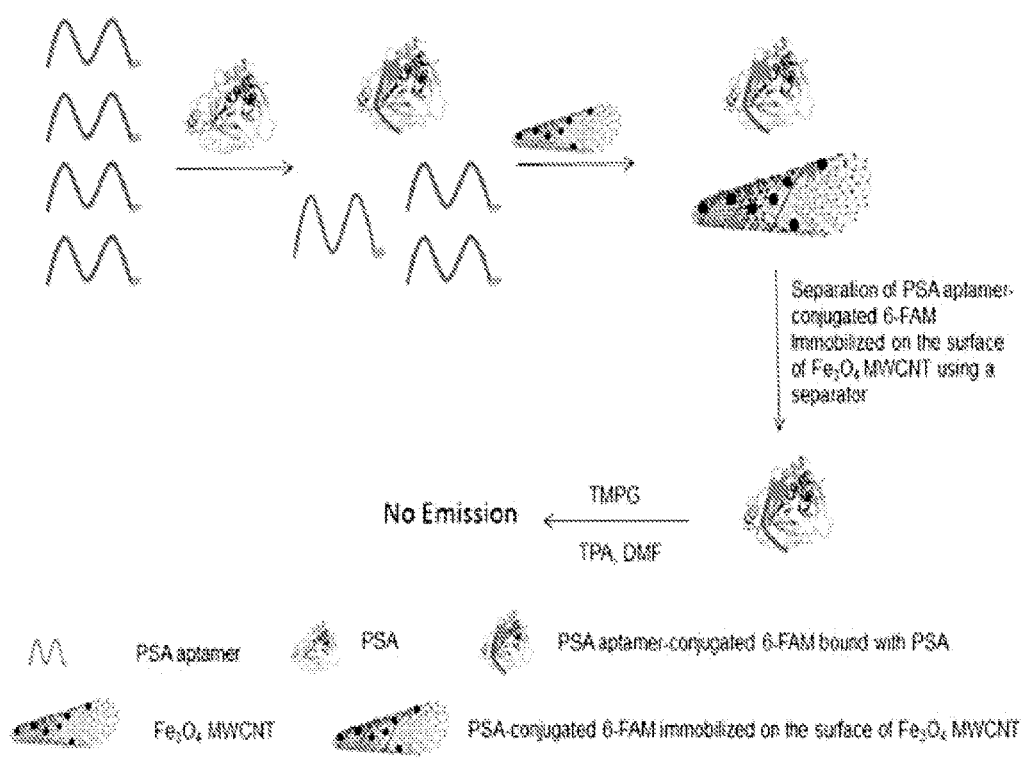
FIG. 9: Procedure to measure CL emission of PSA aptamer bound with PSA antigen in guanine chemiluminescence reaction.
Figure 10:
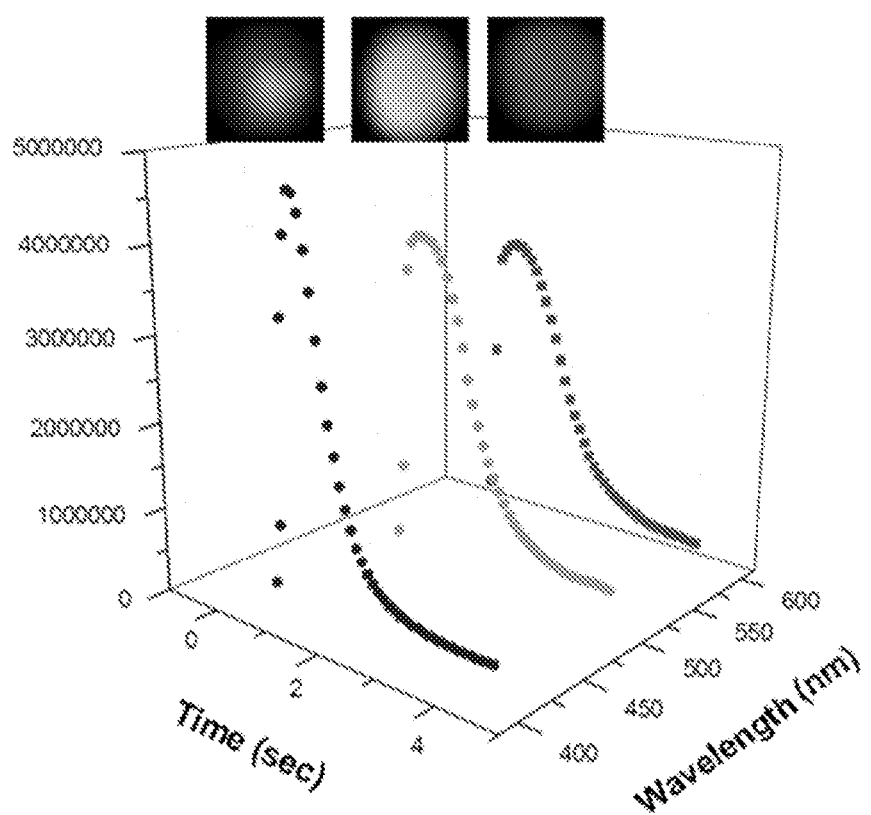
FIG. 10: 3-D spectrum of CL emitted in a sample containing aptamers conjugated with three different fluorescent dyes. In order to observe bright CL emission, no analytes such as food-borne pathogens were added because the brightness of CL is decreased in the presence of analyte based on the principle of CRET between X and analyte.

In order to confirm that PSA aptamer-bound PSA cannot emit CL, diluted magnetic $Fe_3O_4$-graphene oxide or $Fe_3O_4$-carbon nanotubes (50 µl) was added in the centrifuge tube containing PSA and PSA aptamer and incubated for 1 minute. After the incubation, free PSA aptamers immobilized on the surface of magnetic $Fe_3O_4$-graphene oxide or $Fe_3O_4$-carbon nanotubes were removed using a magnetic bar. Then, it was confirmed that PSA aptamer-bound PSA cannot emit light as shown in FIG. 9.

E. Thrombin Quantification in Human Serum Using a Aptasensor with Guanine-CL Detection and Label Free DNA Aptamer Various concentrations of thrombin were prepared in artificial human urine.

DNA aptamer-conjugated 6-FAM (1 µM)(thrombin aptamer=5'-6-FAM-GGTTGGTGTGGTTGG-3', SEQ ID NO: 3) capable of rapidly capturing thrombin was prepared in Tris-HCl buffer (pH 7~8.5).

0.02 M TPA was prepared in deionized water.

1 mM TMPG was prepared in DMF.

Procedure

Analytical sample (50 µl) containing a certain concentration of Thrombin was mixed with thrombin aptamer (50 µl) in a 1.5-ml centrifuge tube and incubated for 10 minutes.

The mixture (20 µl) was inserted into a borosilicate test tube containing TPA (10 µl).

TMPG (100 µl) was added in the test tube and measured immediately CL emission for 20 seconds using a luminometer.

Results

Figure 6:
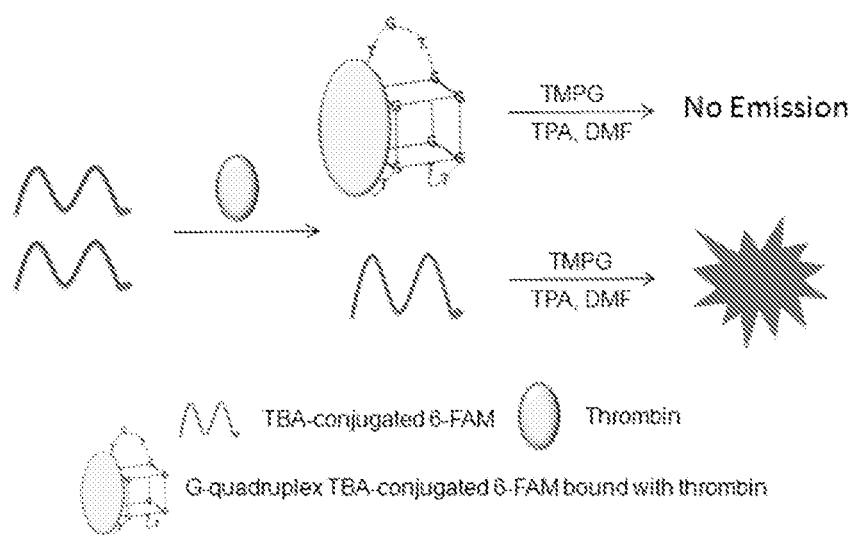
FIG. 6: Principle of G-quadruplex thrombin aptasensor with Guanine-CL detection
Figure 7:
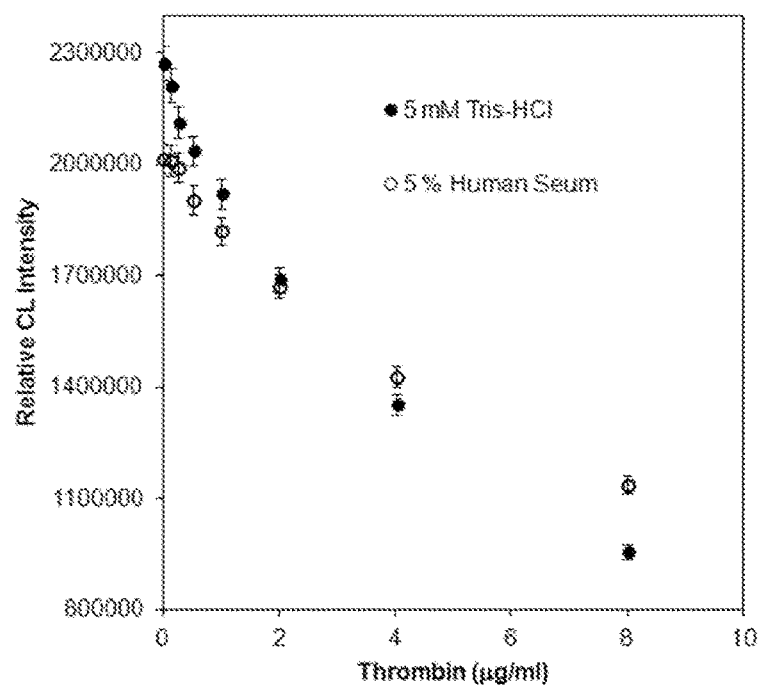
FIG. 7: Calibration curves capable of quantifying thrombin

With the increase of thrombin, CL emission was decreased because G-quadruplex DNA aptamers bound with thrombin cannot emit light, whereas free thrombin aptamer can emit bright light as shown in FIG. 6. Using the calibration curves shown in FIG. 7, trace levels of thrombin in human serum or buffer was quantified.

F. Quantification of Food-borne Pathogens in a Sample Using Guanine-CL Reaction

Various concentrations of preheated food-borne pathogens (e.g., *Salmonella*, *E. Coli* O157: H7, *Listeria*) was prepared in deionized water.

*Salmonella* aptamer-conjugated pacific blue (1 µM) (5'-Pacific blue-GGGAGCTCAGAATAAACGCT-CAAGGGCAGGTGTTATGTGTACTGCTACAGTGTG GTTGTTCGACATGAGGCCCGGAC-3', SEQ ID NO: 4), *E. Coli* O157: H7-conjugated fluorescein (1 µM) (5'-CCG-GACGCTTATGCCTTGCCAT CTACAGAGCAGGTGT-GACGG-fluorescein-3', SEQ ID NO: 5), and *Listeria*-conjugated Cy3.5 (1 µM)(5'-Cy3.5-GGGG GGCCTAGACTAGGGGGAGAGGGTGGGACGGT-3', SEQ ID NO: 6) were prepared in tris-HCl buffer (pH 7~8.5).

0.02 M TPA was prepared in deionized water.

1 mM TMPG was prepared in DMF.

Procedure

Analytical mixture (50 µl) containing a certain concentration of *Salmonella*, *E. Coli* O157: H7, and *Listeria* was mixed with three specific aptamers (50 µl), capable of capturing *Salmonella, E. Coli* O157: H7, and *Listeria* in a 1.5-ml centrifuge tube and incubated for 30 minutes.

The mixture (20 μl) was inserted into a borosilicate test tube containing TPA (10 μl).

TMPG (100 μl) was added in the test tube and measured immediately CL emission for 20 seconds using a luminometer.

Figure 8:
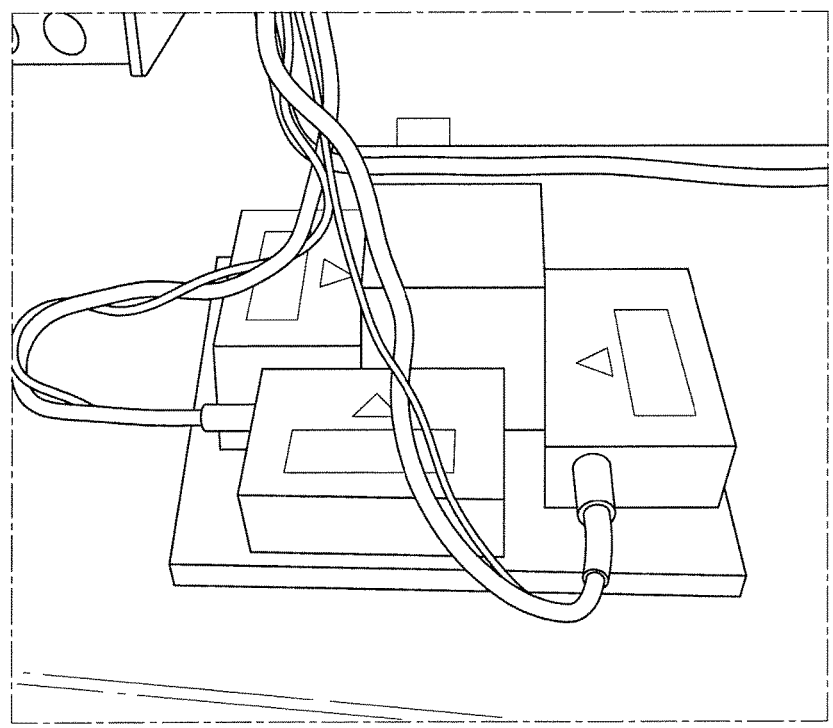
FIG. 8: Luminometer with three photomultiplier capable of simultaneously quantifying three different food-borne pathogens in a sample.

In order to simultaneously quantify three different food-borne pathogens in a sample, a home-made luminometer having three photomultiplier tubes (PM-tube) as shown in FIG. 8 was used. Each PM-tube has a specific filter to measure CL emitted at a specific emission range. Using the luminometer, it was possible to simultaneously sensing trace levels of food-borne pathogens in a sample. The result indicates that Guanine-CL can be applied to simultaneously quantify multiple targets in a sample.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit.

At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for generating chemiluminescence comprising:
mixing phenylglyoxal or a derivative thereof with a nucleic acid sequence comprising guanine complexed to a fluorescent label in the presence of a base to form

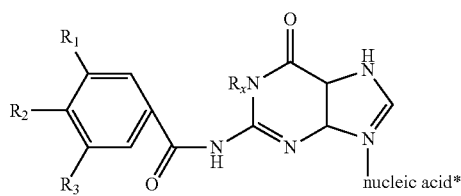

wherein $R_x$ is and wherein $R_1$, $R_2$, and $R_3$ are each independently H, linear or branched $C_1$-$C_6$ alkyl, oxy, or $C_1$-$C_6$ alkoxy groups, wherein the base is a tetra-n-propyl ammonium (TPA) derivative, and wherein the nucleic acid is a natural or artificial deoxyribonucleic acid or ribonucleic acid, and the compound resonates with the conjugated fluorescent label to produce chemiluminescence.

2. The method according to claim 1, wherein the concentration of the base is 5-100 mM.

3. A method for generating chemiluminescence comprising:
mixing phenylglyoxal or a derivative thereof with a nucleic acid sequence comprising guanine complexed to a fluorescent label in the presence of a base to form

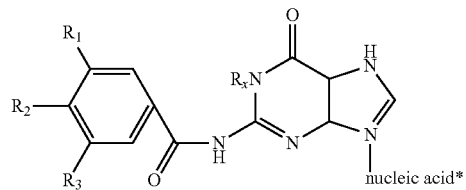

wherein $R_x$ is and wherein $R_1$, $R_2$, and $R_3$ are each independently H, linear or branched $C_1$-$C_6$ alkyl, oxy, or $C_1$-$C_6$ alkoxy groups, wherein the base is tetra-n-propyl ammonium phosphate, and wherein the nucleic acid is a natural or artificial deoxyribonucleic acid or ribonucleic acid, and the compound resonates with the conjugated fluorescent label to produce chemiluminescence.

4. The method according to claim 1, wherein the fluorescent label is selected from the group consisting of: pacific blue, fluorescein, 6-FAM, Cy 3, Cy 3.5, Cy 5, Cy 5.5, HEX, TET, VIC, NED, JOE, ROX, Texas Red, Rhodamine Green, Rhodamine Red, TEX 615.

* * * * *

SEQUENCE LISTING

```
<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: Aptamer

<400> SEQUENCE: 1
ggttggtgtg gttgg                                                        15

<210> SEQ ID NO 2
<211> LENGTH: 35
<212> TYPE: DNA
<213> ORGANISM: Artificial Sequence
<220> FEATURE:
<223> OTHER INFORMATION: PSA aptamer

<400> SEQUENCE: 2
tttttaatta aagctcgcca tcaaatagct ggggg                                  35

<210> SEQ ID NO 3
<211> LENGTH: 15
<212> TYPE: DNA
<213> ORGANISM: Artificial Sequence
<220> FEATURE:
<223> OTHER INFORMATION: thrombin aptamer

<400> SEQUENCE: 3
ggttggtgtg gttgg                                                        15

<210> SEQ ID NO 4
<211> LENGTH: 77
<212> TYPE: DNA
<213> ORGANISM: Artificial Sequence
<220> FEATURE:
<223> OTHER INFORMATION: Salmonella aptamer

<400> SEQUENCE: 4
gggagctcag aataaacgct caagggcagg tgttatgtgt actgctacag tgtggttgtt       60
cgacatgagg cccggac                                                      77

<210> SEQ ID NO 5
<211> LENGTH: 42
<212> TYPE: DNA
<213> ORGANISM: Artificial Sequence
<220> FEATURE:
<223> OTHER INFORMATION: E.Coli aptamer

<400> SEQUENCE: 5
ccggacgctt atgccttgcc atctacagag caggtgtgac gg                          42

<210> SEQ ID NO 6
<211> LENGTH: 35
<212> TYPE: DNA
<213> ORGANISM: Artificial Sequence
<220> FEATURE:
<223> OTHER INFORMATION: Listeria aptamer

<400> SEQUENCE: 6 gggggggccta gactaggggg agagggtggg acggt                                 35
```